(12) United States Patent
Nagle et al.

(10) Patent No.: US 6,498,353 B2
(45) Date of Patent: *Dec. 24, 2002

(54) MICROFLUIDIC DEVICES AND SYSTEMS INCORPORATING INTEGRATED OPTICAL ELEMENTS

(75) Inventors: Robert Nagle, Mountain View, CA (US); Colin B. Kennedy, Greenbrae, CA (US)

(73) Assignee: Caliper Technologies, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/038,525

(22) Filed: Oct. 24, 2001

(65) Prior Publication Data
US 2002/0092973 A1 Jul. 18, 2002

Related U.S. Application Data

(63) Continuation of application No. 09/595,728, filed on Jun. 16, 2000, now Pat. No. 6,316,781, which is a continuation of application No. 09/030,535, filed on Feb. 24, 1998, now Pat. No. 6,100,541.

(51) Int. Cl.[7] .............................................. G01N 15/06
(52) U.S. Cl. ....................................... 250/573; 250/216
(58) Field of Search ................................ 250/573, 216, 250/576, 574; 356/246, 244; 422/99, 104, 108, 100; 204/603, 601, 612, 297 R

(56) References Cited

U.S. PATENT DOCUMENTS

| 3,641,354 A | 2/1972 | De Ment |
| 4,390,403 A | 6/1983 | Batchelder |
| 4,481,531 A | 11/1984 | Warde et al. |
| 4,816,695 A | 3/1989 | Lavin |
| 4,857,273 A | 8/1989 | Stewart |
| 4,908,112 A | 3/1990 | Pace |
| 5,126,022 A | 6/1992 | Soane et al. |
| 5,228,969 A | 7/1993 | Hernandez |
| 5,415,727 A | 5/1995 | Gal et al. |
| 5,498,392 A | 3/1996 | Wilding et al. |

(List continued on next page.)

FOREIGN PATENT DOCUMENTS

| EP | 0 708 331 | 4/1996 |
| WO | WO 96/04547 | 2/1996 |
| WO | WO 97/02357 | 1/1997 |

OTHER PUBLICATIONS

Dasgupta, P.K. et al., "Electroosmosis: A Reliable fluid Propulsion System for Flow Injection Analysis," *Anal. Chem.* 66:1792–1798 (1994) Month Unknown.

Jacobson, S.C. et al., "Fused Quartz Substrates for Microchip Electrophoresis," *Anal. Chem.* 67:2059–2063 (1995) Month Unknown.

Manz, A. et al., "Electroosmotic pumpgin and electrophoretic separations for miniaturized chemical analysis systems," *J. Micromech. Microeng.* 4:257–262 (1994) Month Unknown.

Nussbaum, Ph. et al., "Design, fabrication and testing of microlens arrays for sensors and microsystems," *Pure Appl. Opt.* 6:617–636 (1997) Month Unknown.

(List continued on next page.)

*Primary Examiner*—Que T. Le
(74) *Attorney, Agent, or Firm*—Andrew L. Filler; Matthew B. Murphy

(57) ABSTRACT

The present invention provides microfluidic devices and systems that utilize optical detection systems, and where one or more light altering optical elements are integrated into the body structure of the microfluidic device. The resulting devices perform at least a portion of the optical manipulations used in the optical detection method employed.

23 Claims, 3 Drawing Sheets

U.S. PATENT DOCUMENTS

| | | | |
|---|---|---|---|
| 5,554,340 A | | 9/1996 | Lackie |
| 5,559,596 A | | 9/1996 | Mersch |
| 5,571,410 A | | 11/1996 | Swedberg et al. |
| 5,585,069 A | | 12/1996 | Zanzucchi et al. |
| 5,593,838 A | | 1/1997 | Zanzucchi et al. |
| 5,603,351 A | | 2/1997 | Cherukuri et al. |
| 5,635,358 A | | 6/1997 | Wilding et al. |
| 5,637,469 A | | 6/1997 | Wilding et al. |
| 5,867,266 A | | 2/1999 | Craighead |
| 5,876,675 A | | 3/1999 | Kennedy |
| 6,100,541 A | * | 8/2000 | Nagle et al. .......... 204/603 |
| 6,251,343 B1 | * | 6/2001 | Dubrow et al. .......... 422/100 |
| 6,316,781 B1 | * | 11/2001 | Nagle et al. .......... 250/216 |

OTHER PUBLICATIONS

Ramsey, J.M. et al., "Microfabricated chemical measurement systems," *Nature Med.* 1:1093–1096 (1995) Month Unknown.

Seiler, K. et al., "Planar Glass Chips for Capillary Electrophoresis: Repetitive Sample Injection, Quantitation, and Separation Efficiency," *Anal. Chem.* 65:1481–1488 (1993) Month Unknown.

Seiler, K. et al., "Electroosmotic Pumping and Valveless Control of Fluid Flow within a Manifold of Capillaries on a Glass Chip," *Anal. Chem.* 66:3485–3491 (1994) Month Unknown.

Degrandpre, M.D. et al., "Thin Film Planar Waveguide Sensor for Liquid Phase Absorbance Measurements" *Anal. Chem.* (1990) 62(18):2012–2013 Month Unknown.

* cited by examiner

MICROFLUIDIC DEVICES AND SYSTEMS INCORPORATING INTEGRATED OPTICAL ELEMENTS

CROSS-REFERENCE TO RELATED APPLICATIONS

This application is a continuation of U.S. patent application Ser. No. 09/595,728, filed Jun. 16, 2000, now U.S. Pat. No. 6,316,781, which is a continuation of U.S. patent application Ser. No. 09/030,535, filed Feb. 24, 1998, now U.S. Pat. No. 6,100,541, the disclosures of which are incorporated herein in their entirety.

BACKGROUND OF THE INVENTION

The use of microfluidic technology has been proposed for use in a number of analytical chemical and biochemical operations. These technologies provide advantages of being able to perform chemical and biochemical reactions, macromolecular separations, and the like, that range from the simple to the relatively complex, in easily automatable, high-throughput, low-volume systems. In particular, these systems employ networks of integrated microscale channels in which materials are transported, mixed, separated and detected. The small size of these systems allows for the performance reactions at substantially greater rates, and with substantially less reagent volume. Further, the development of sophisticated material transport systems has permitted the development of systems that are readily automatable and highly reproducible.

Because of their small size, microfluidic systems have typically required the use of relatively sophisticated detection systems to monitor the progress and results of the operation being performed by the system. In particular, as noted above, the extreme small scale of some microfluidic systems results in very small volumes of reagents, samples and the like, being used. Consequently, the amount of material that can be ultimately detected, e.g., using an optical detection system, is also very small. In order to address these issues, detection systems have become more sophisticated to either boost the detectable signal produced from material sought to be detected, increase the sensitivity of the instrumentation, or a combination of the two. For example, microscopes equipped with photomultipliers enhance the ability to detect fluorescently labeled materials within microscale channels. Further, the use of laser-induced fluorescence also enhances the amount of signal produced from these fluorescent materials.

Although these sophisticated detection systems have addressed many of the problems associated with detection in microscale fluidic channels, a number of problems remain, such as difficulty in optimally aligning these instruments, the cost and sophistication of providing robust optics for such systems and the like. Further, as the number of applications for microfluidic systems increases, it will include a similar increase in the type of optical detection systems to be used. The use of specifically tailored detection systems for each different application will present a likely prohibitive cost barrier. The present invention addresses many of the problems outlined above, as well as others.

SUMMARY OF THE INVENTION

The present invention provides microfluidic devices for use in performing analytical operations that employ optical detection systems. In particular, the present invention provides microfluidic devices, and systems incorporating such devices, which have at least one component of the optical detection system as a part of the microfluidic device.

In a first aspect, the present invention provides a microfluidic device which comprises a body structure having a microscale channel disposed therein. The device includes a light altering optical element integrated into the body structure adjacent to the microscale channel, whereby at least a portion of light passing from or to the microscale channel is transmitted through the light altering optical element. In preferred aspects, the body structure of the device comprises a first planar substrate having at least first and second opposing planar surfaces, the microscale channel being fabricated into the first planar surface of the first substrate, and the light altering optical element being fabricated into the second planar surface of the first substrate adjacent to the microscale channel in the first planar surface. Also included is a second planar substrate overlaying the first surface of the first planar substrate.

In an alternate aspect, a third substrate layer is provided having at least a first planar surface and a second surface. The first planar surface of the third substrate layer is bonded to one of the second planar surface of the first planar substrate or the second planar surface of the second planar substrate. The third substrate also includes a light altering optical element fabricated into the second surface of the third substrate.

In still another related aspect, the present invention also provides a microfluidic device, which comprises a body structure having an interior portion and an exterior portion. At least a first microscale channel is disposed within the interior portion of the body structure. A detection window is provided disposed on the exterior portion of the body structure, whereby the detection window provides optical access to the at least one microscale channel. In this aspect, the detection window comprises a light altering optical element integrated into the body structure.

Also provided by the present invention are microfluidic systems, which comprise a microfluidic device comprising a body structure, at least a first microscale channel disposed in the body structure, a transparent region in the body structure, the transparent region including a light altering optical element integrated into the body structure. The systems of the invention alo typically comprise an optical detector disposed adjacent to the detection window. The optical detector comprises an objective lens for collecting an optical signal transmitted from the microscale channel via the light altering optical element, and a light detector for measuring an amount of light collected.

DETAILED DESCRIPTION OF THE INVENTION

I. General

Figure 1:
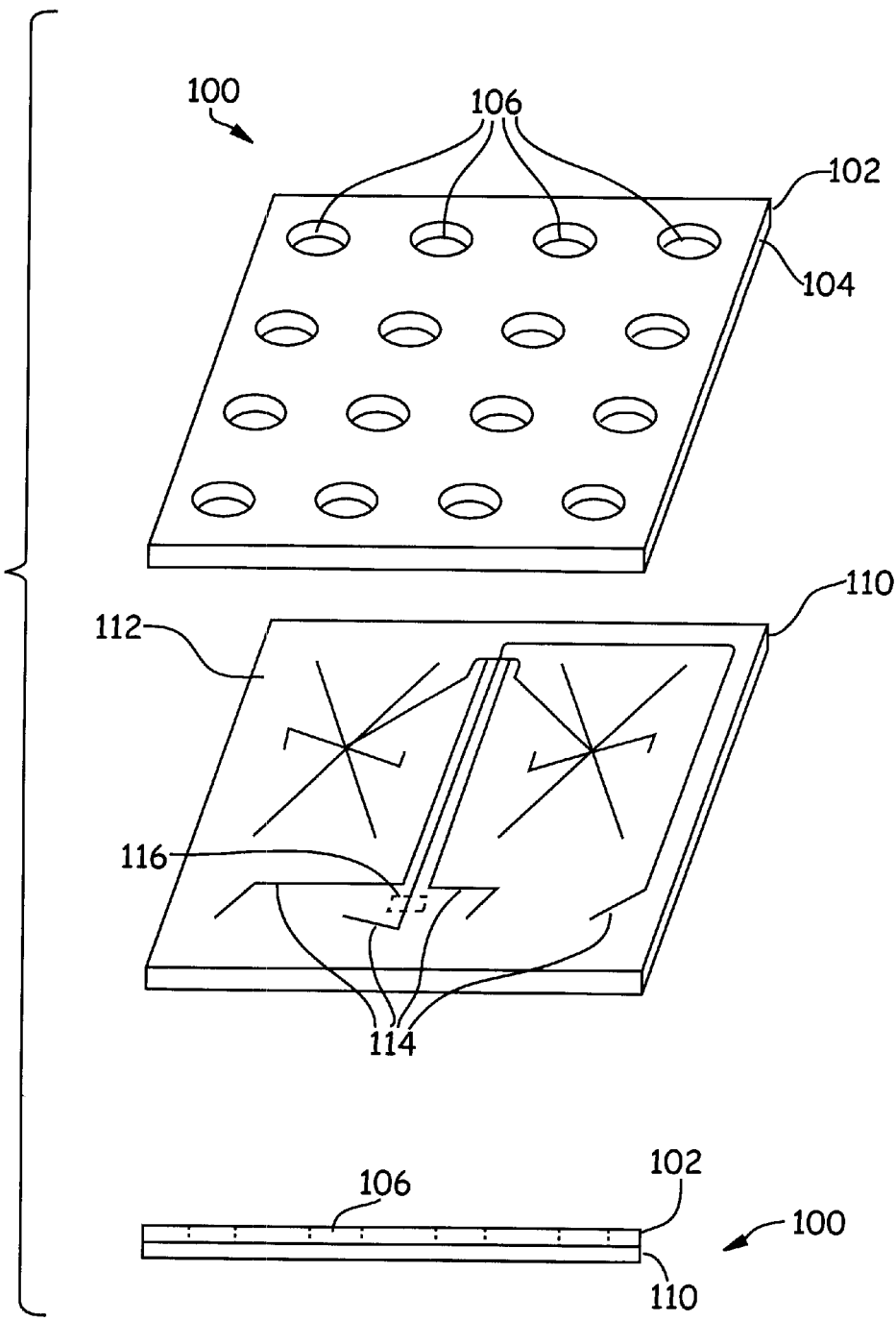
FIG. 1 schematically illustrates a general microfluidic device having abody structure that incorporates multiple substrate layers.

The present invention generally provides microfluidic devices that have one or more optical elements that are employed in the use of such devices, as an integral portion of the device itself, e.g., incorporated into or attached to the body structure of the device. These devices address a number of the problems that are associated with optical detection systems that have been used in conjunction with microfluidic systems.

Typical microfluidic systems employ a body structure or substrate that has at least one microscale channel disposed within it. Examples of such systems range from simple tubular capillary systems, e.g., fused silica capillaries, to more complex planar devices that can have from one to several intersecting channels disposed therein, i.e., between at least two planar substrate layers. Microfluidic systems generally have a broad range of uses including separation and characterization of macromolecular species, e.g., proteins and nucleic acids, see e.g., U.S. Pat. No. 5,699,157, screening assay platforms, e.g., drug screening, diagnostics, etc. See, e.g., commonly owned Published PCT Application No. WO 98/00231, each of which is incorporated herein by reference in its entirety for all purposes.

In many cases, microfluidic systems utilize optical detection systems in the performance of their analytical and/or synthetic functions. These optical detection systems generally require the presence within the microfluidic system of an optical access point, e.g., a detection window, whereby light energy can be transmitted to and from one or more channels of the system. Such detection windows are typically made up of at least a transparent region of the body structure of the device. This is a simple solution where body structures are fabricated from transparent substrates, e.g., glass, quartz or transparent polymers.

In operation, an optical detector is placed adjacent the transparent region of the device, where it collects optical signals from the channels of the device. The optical detector, for its part, typically includes a number of optical elements to aid in the reception, transmission and detection of the optical signal. Many of these optical elements are capable of affecting or altering the light that passes through them. As used herein, a "light altering" capability, is the ability of an optical element to alter the amount, spectrum, direction, path, or polarity of light passing through that optical element. Some examples of such light altering elements include lenses, optical gratings, filters, beam splitters, mirrors, optical coatings, e.g., antireflective coatings, and the like. Optical detectors also often include light sources, i.e., lasers, LEDs, high intensity lamps, etc., for directing light at the channel for, e.g., fluorescent, absorbance-based or colorimetric detection schemes.

While the optical detection systems described above have proven very useful in the operation of microfluidic systems, these detection systems have a number of drawbacks. For example, because microfluidic systems utilize extremely small-scale channels in which detection occurs, alignment of an external detector at the detection point becomes a difficult proposition. In particular, one must align an external detector with precision in order to capture optimal signal from channels that typically range from about 10 to about 100 $\mu$m wide. Alignment of the detection optics is generally carried out by scanning the detector across the detection window, e.g., in the x-y axes, until an optimal signal indicative of alignment is achieved. This type of alignment, however, is very time consuming, and in the case of automatic alignment systems, has an additional cost in terms of the required equipment, and the like. A similar method is employed in focusing these detection systems, where the detector is moved along the z-axis, e.g., closer to and further from the device, until an optimal signal is received.

Similarly, because there is typically an air gap between the substrate or device and the first optical element of the detector, the light delivery and collection efficiencies of such systems are also reduced.

In addition to problems with alignment and light collection efficiency, optical detection systems also must typically be tailored to the particular application being performed within the microfluidic device. For example, fluorescence based detectors typically must include high intensity light sources, dichroic filters, beam splitters, photomultipliers and the like, to excite fluorescent species in the channel, separate the emitted fluorescence from the reflected excitation light, and measure the emitted fluorescence. Additionally, the combination of different filters, dichroics and beam splitters must be tailored further for the specific fluorescent spectra of the operation that is being performed within the system, e.g., depending upon the fluorescent label, or combination of fluorescent labels used. Different detection schemes, e.g., absorbance, i.e., U.V. or colorimetric, require a different set of optical elements, by virtue of having little or no need for light-separation optics. The need for optical systems that are specifically tailored for different detection schemes, assays or the like, further escalates the costs associated with performing the full range of optical analyses in microfluidic systems.

In accordance with the present invention, microfluidic devices are provided where the body structure is fabricated to include at least one light altering optical element. The incorporation of such elements into the body structure of the device permits the use of more universal detection systems, as the microfluidic device itself meets many of the specific optical requirements for its particular application. Additionally, incorporation of optical elements also can facilitate alignment of microfluidic devices within the detection system, by providing a pre-aligned lens. Further, the inclusion of integrated optical elements provides enhanced efficiencies in terms of light collection and delivery. For example, incorporation of a lens molded into the body structure or substrate of the device allows for a numerical aperture (NA) that can be greater than 1, and light delivery and collection efficiencies for lenses are both proportional to $(NA)^2$. Similarly, losses due to total internal reflection are minimized.

In a further advantage, the incorporation of certain optical elements in the mass produced microfluidic devices can provide advantages in terms of cost, over the inclusion of more robust versions of the same elements in the detection instrumentation.

II. Integrated Optical Components

As noted above, the microfluidic devices of the present invention typically comprise a body structure having one or more microscale channels disposed therein. As used herein, the term "microscale or microfluidic channel" refers to a fluid channel or conduit that has at least one cross-sectional dimension, e.g., width, depth or diameter, of between about 0.1 and 500 $\mu$m. Preferably, such channels have at least one cross sectional dimension in the range of from about 1 to about 200 $\mu$m and more preferably, from about 5 to about 100 $\mu$m.

In preferred aspects the microfluidic devices described herein are planar in structure, although non-planar device structures, e.g., tubular structures, are also possible within the scope of the present invention. In the planar device structures, the body portion of the device is typically fabricated from one or more planar substrate layers. An example of this planar layered structure is illustrated in FIG. 1. In particular, the body of the microfluidic device 100 includes a first planar substrate 110 that is fabricated with a series of grooves and/or depressions 114 in its upper surface 112. These grooves or depressions correspond to the channel/chamber geometry of the finished device. A second planar substrate 102 is then overlaid and its lower surface 104 is bonded to the surface of the first substrate to seal and define the last wall of the channels/chambers of the device. Optional ports/reservoirs 106 are provided in the body structure and in fluid communication with the channels of the device, to provide fluid and/or electrical access to the channels. These ports/reservoirs are generally provided as apertures disposed through the upper substrate layer 102, e.g., connecting surface the upper surface with lower surface 104, whereby they will fluidly communicate with one or more of the sealed channels 114. These devices also typically include an optical detection window 116 to permit measurement of optical signals from the channels. Examples of microfluidic devices incorporating this planar body structure are described in substantial detail in Published PCT Application No. WO 98/00231, WO 98/00705, and U.S. patent application Ser. No. 08/845,754, filed Apr. 25, 1997, each of which is incorporated herein by reference.

Typically, these microfluidic devices employ fluid or material direction systems to transport fluids or other materials through and among the channels and chambers of the device in order to perform the combinations, separations or other operations in carrying out a given analysis. Examples of such transport systems include pneumatically or hydraulically driven systems, e.g., as described in published PCT Application No. 97/02357, systems incorporating microfabricated pumps and/or valves, and, in preferred aspects, electrokinetic material transport systems, e.g., as described in Published PCT Application No. 96/04547.

As noted above, the microfluidic devices of the present invention include an optical detection window disposed in the body structure of the device adjacent to one or more of the included microscale channels. In accordance with the present invention, these optical detection windows include at least one light altering optical element integrated into the body structure of the device. As used herein, the phrase "integrated into" refers to optical elements that are either fabricated into the body structure or are attached to the body structure such that the optical element(s) and body structure form(s) a single integrated unit. The light altering optical element is capable of transmitting light while altering the amount, spectrum, polarity or path of the light transmitted therethrough. The integrated optical element may be fabricated into, or attached to the body structure, as described in greater detail below. Examples of particularly preferred optical elements include lenses (e.g., spherical, aspheric, fresnel, binary) to perform magnifying, demagnifying, collimating, light delivery, light collection or focusing functions, optical filters (spatial or wavelength selecting), optical gratings, optical coatings (e.g., dichroic, antireflective, reflective), beam splitters, waveguides, TIR mirrors, polarizers and the like. For a discussion of these optical elements, see, e.g., Handbook of Optics, volume II, (1995 McGraw-Hill), which is incorporated herein by reference in its entirety for all purposes.

Figure 2:
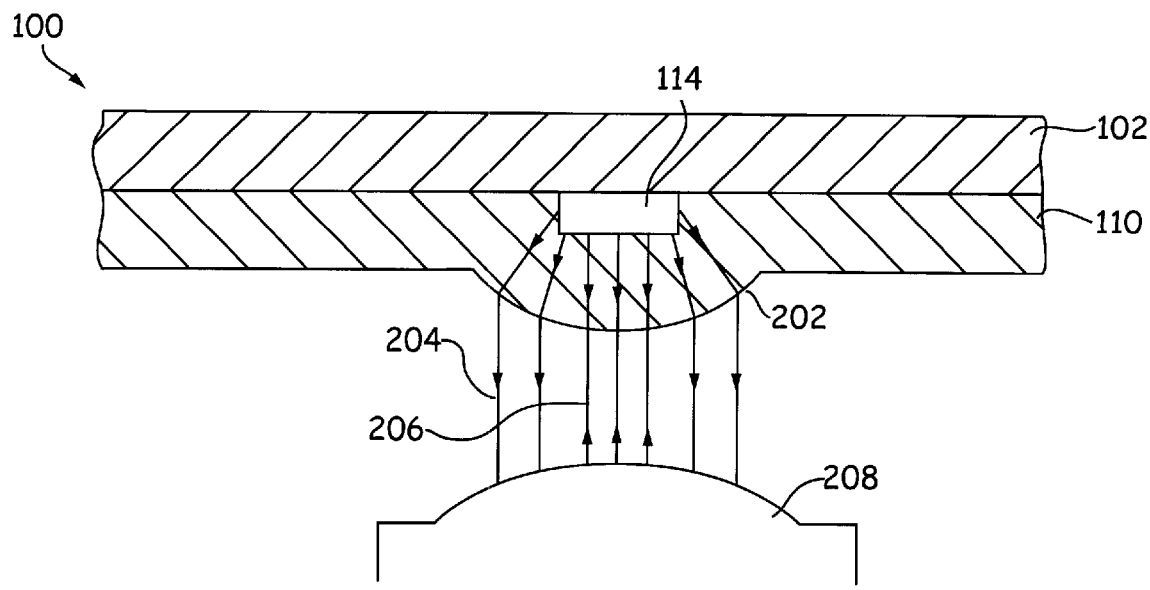
FIG. 2 is a schematic illustration from a side view of a microfluidic device having a light altering optical element integrated into the body structure of the device.

In one aspect of the present invention, the optical elements described above are typically fabricated into one of the substrate layers that makes up the body structure of the device, e.g., the first or second substrate layer described previously. A schematic illustration of a device incorporating an optical element in one of the layers of the body structure is shown in FIG. 2. As shown, the device 100 includes a first planar substrate layer 110 and a second planar substrate layer 102. The channel(s) of the device 114 (shown in cross-section) are fabricated into the first substrate layer 110 as a groove or depression. The second substrate layer 102 is overlaid and bonded to the first substrate 110 to seal the channel(s) 114. An optical element, shown in FIG. 2 as collimating lens 202 is also shown fabricated into the first substrate layer 110 at the point of the optical detection window (116 from FIG. 1). The lens 202 is positioned so as to permit transmission of an optical signal from the channel 204, as well as permitting transmission of external light energy 206 into the channel, e.g., for use in fluorescence or absorbance based detection. In particular, as shown, lens 204 is illustrated as a collimating lens, whereby light emitted from, or reflected by the contents of the channel 114, passes through lens 204 and is collimated, so as to be efficiently collected by the optical detection system, as represented by objective lens 208. As shown, the collimating lens 204 allows more light to be gathered by the objective lens 208, as well as allows simpler alignment of the objective lens, e.g., over larger lens 204, as opposed to the much smaller channel 114.

As illustrated, the optical element is fabricated into the same substrate into which was fabricated the fluidic elements of the device, e.g., the microscale channels. In many cases, this permits the fabrication of both the fluidic and optical elements in the same fabrication step. In particular, where polymeric substrates are used in the body structure of the overall device, the same fabrication techniques used in producing the fluidic elements, e.g., injection molding, embossing, and the like, are also used to fabricate structurally defined optical elements. Although not shown, it will be appreciated that the optical element can also be fabricated into the upper substrate, depending upon the orientation of the optical detector relative to the device, i.e., above or below.

In an alternate aspect, the microfluidic devices of the present invention include an additional substrate layer, i.e., in addition to the at least first and second substrate layers, that incorporates the light altering optical element or elements, but does not necessarily define any of the fluidic elements of the microfluidic device. The additional substrate layer is typically attached to the body structure of the microfluidic device, e.g., by bonding, clamping, or other substantially secure coupling methods.

Figure 3:
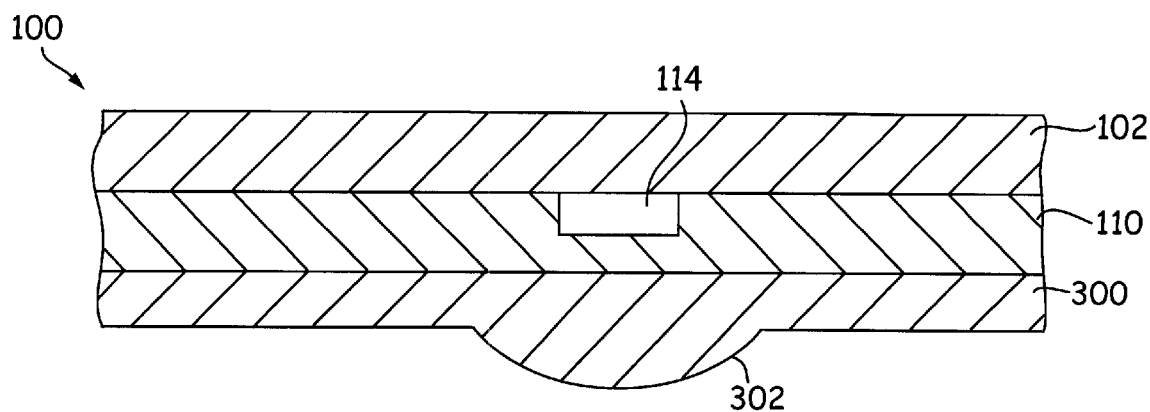
FIG. 3 is a schematic illustration of an alternative device, having a light altering optical element integrated into the body structure of the device through the incorporation of an additional substrate layer that includes the optical element.

An example of a microfluidic device incorporating this alternate structure is illustrated in FIG. 3. Again, as shown, the device 100 includes a body structure that is made up of at least two planar substrate layers 102 and 110. The channels 114 of the device (shown in cross-section), are again fabricated into the surface 112 of substrate 110. In the aspect illustrated in FIG. 3, a third substrate layer 300 is bonded or attached to the bottom surface of lower substrate 110. This third substrate layer includes a light altering optical element, shown as lens 302, fabricated into the third substrate layer 300. The use of one or more auxiliary layers for the addition of optical elements to the microfluidic device body structure, permits a more generalized manufacturing method for the fluidic structures of the device, e.g., channels, ports and the like. Specifically, a single type of channel and port geometry, e.g., layout, can be used in performing a number of different types of analyses, each requiring somewhat different optics in its detection scheme.

As such, each different type of device can be provided with any of a number of different optical elements by simply attaching an appropriate third substrate layer having the appropriate optical element fabricated into it. In this aspect, the present invention provides still a further level of interchangeability, namely, interchangeability of fluidic elements, as well as the interchangeability of the optical detectors. Examples of a cover layers that are readily attached to the body structure of the device are described in commonly owned U.S. patent application Ser. No. 09/028, 965, entitled "Microfluidic Devices and Systems Incorporating Functional Cover Layers," filed of even date, which is incorporated herein in its entirety for all purposes. Specifically, the optical elements described herein are readily included in a functional cover layer that is attached to the body structure of the device.

Fabrication of the light altering optical element into the surface of one of the substrate layers of the body structure is generally carried out by any of a number of well known manufacturing techniques, depending upon the type of optical element that is being used. For example, substrate layers incorporating structurally defined optical elements, e.g., lenses, optical gratings, etc., are optionally fabricated from polymeric materials, thus allowing production of the optical element as a portion of the overall fabrication process. Specifically, the polymeric substrates incorporating these optical elements may be produced using, e.g., injection molding, embossing, LIGA and related processes. This is particularly useful where the substrates that make up the microfluidic elements of the device also are fabricated from polymeric materials, so that a single mold can define/provide for both the microfluidic and optical elements of the microfluidic device. In particular, a mold for the planar substrate provides on one surface, features that define the fluid channels of the overall device, and on the opposing surface, features that define the optical element. These polymer fabrication techniques are equally applicable to substrate layers that are used simply to add optical elements to the body structure of the device.

The use of polymeric materials in the fabrication of microfluidic devices is described in detail in U.S. patent application Ser. No. 08/843,212, filed Apr. 14, 1997, and incorporated herein by reference in its entirety for all purposes. Examples of suitable polymeric materials for use in fabrication of the substrate layers of the microfluidic devices described herein include, e.g., polydimethylsiloxanes (PDMS), polymethylmethacrylate (PMMA), polyurethane, polyvinylchloride (PVC), polystyrene, polysulfone, polycarbonate and the like.

In some cases, the microfabrication methods described for use in fabrication of the channel structures in non-polymer substrates are optionally used in fabricating optical elements into the surface of the substrates, e.g., in the case of silica substrates. For example, optical gratings, binary optics or fresnel lenses are optionally etched into the surface of the substrate using the lithographic methods described herein, e.g., photolithography, wet chemical etching, and the like. See Handbook of Optics, vol II pp 7.18–7.21 and 8.1–8.18 (McGraw-Hill 1995), previously incorporated herein by reference.

In a number of instances, substrate layers incorporating the light altering optical element are fabricated from, or alternatively, coated with materials that have the desired light altering characteristics. For example, in the case of optical filters, one or more substrate layers in the body structure may be coated with materials that will transmit light falling within a desired wavelength range. Examples of such coatings include standard interference-type filters made form periodic layers of materials with different indices of refraction, and controlled thicknesses.

Figure 4:
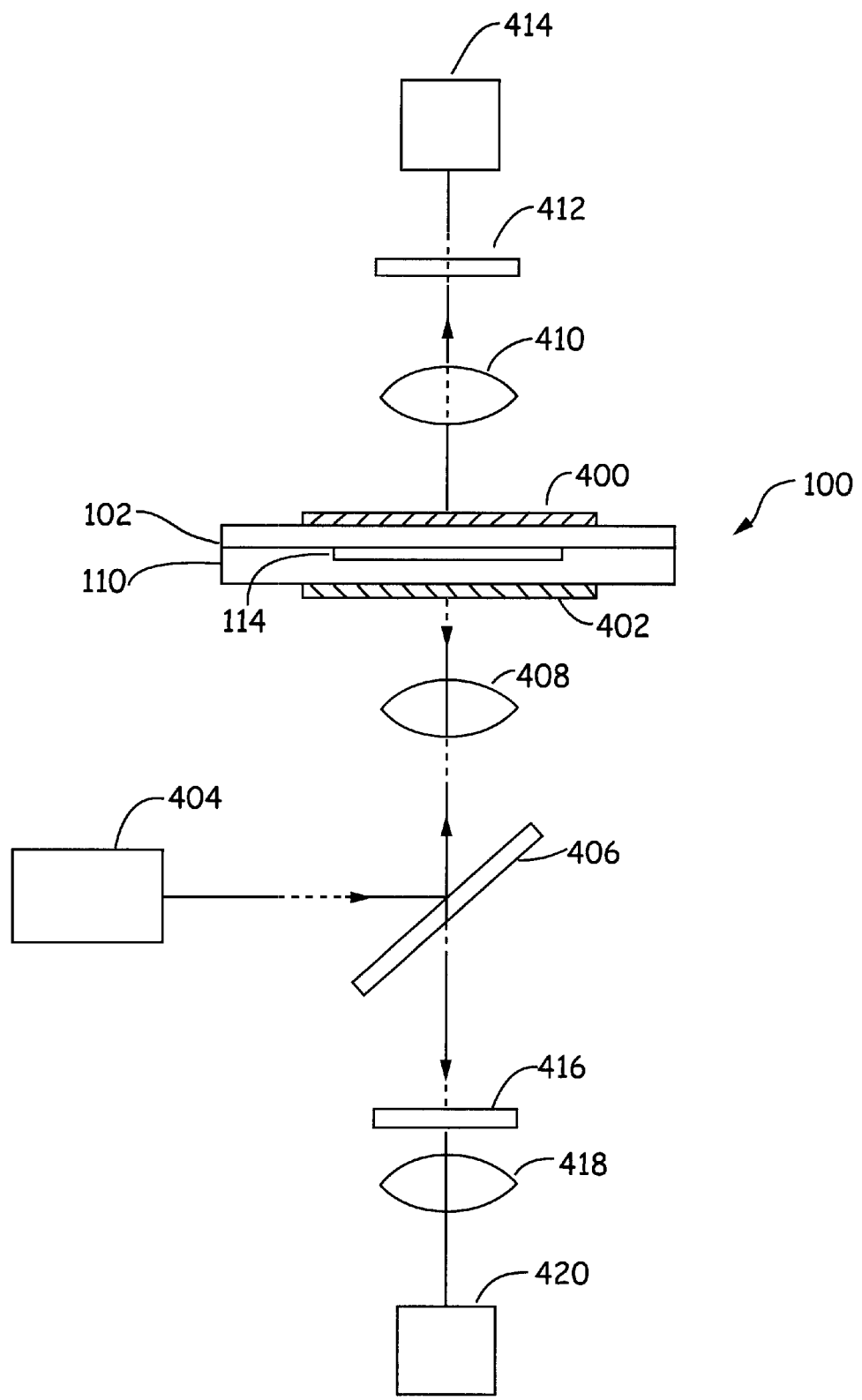
FIG. 4 is a schematic illustration of a system utilizing a microfluidic device that includes polarizers integrated into the overall body structure of the device, and a detector system for use with such device.

Polarizers are also optionally included as the light altering element on the body structure of the microfluidic devices described herein. Such polarizers are typically employed where the overall device is used to perform fluorescence polarization detection based assays run in the channels of the device. An example of a device and system that incorporates integrated polarizers for use in such fluorescent polarization assays is schematically illustrated in FIG. 4.

As shown, the microfluidic device 100, includes a microfluidic channel 114 disposed between upper and lower substrates 102 and 110, respectively. Attached to and integrated with the outer surfaces of the device 100, are polarizers 400 and 402. The overall system into which the microfluidic device is placed, includes a source of unpolarized excitation light 404. Excitation light, e.g., having an appropriate excitation wavelength, from source 404 is directed at dichroic mirror 406 which is typically selected to reflect the excitation light while permitting emitted light, e.g., fluorescence, to pass. Excitation light reflected by the dichroic 406 is focused by lens 408 through polarizer 402 and onto channel 114 whereby it activates any fluorescent species therein. Polarizer 402 is typically oriented in a first plane (e.g., parallel with the plane of the figure sheet) while polarizer 400 is oriented in the perpendicular plane (e.g., perpendicular to the figure sheet). Emitted fluorescence that is in the same plane as polarizer 400 passes through that polarizer and is focused via lens 410, through filter 412, and is detected by photodetector 414, which is optionally a photodiode, PMT or the like. Filter 412 is provided to filter out any excitation light that passes through the device 10 and polarizers 400 and 402. Emitted fluorescence in the same plane as polarizer 402 passes through that polarizer, through lens 408, and through dichroic 406. This fluorescence then passes through filter 416, and is focused via lens 418 onto photodetector 420.

Antireflective coatings are optionally included on the body structure to prevent the adverse effects of internal reflectance of the body structure. Such coatings are generally well known in the art and include, e.g., silicon dioxide ($SiO_2$), magnesium fluoride and the like.

Although illustrated in terms of lenses or coatings, a number of light altering optical elements are optionally incorporated, either alone, or in combination with one or more other optical elements. For example, optical gratings are optionally included to spectrally filter or separate light. Similarly, prisms or beam splitters are optionally included to redirect or separate light directed at or transmitted from the channels of the microfluidic device.

In operation, the microfluidic devices of the present invention are generally used as a portion of a larger microfluidic system. As noted above, such systems typically include a material transport system. For example, in the case of hydraulic or pneumatic material transport systems, the device is typically coupled to an appropriate pressure or vacuum source, either for moving materials through the channels, or for operating microfabricated pumps and valves to move the materials through the channels. Alternatively, the device is coupled with an electrical controller, which applies appropriate currents and/or voltages through the channels of the device to affect electrokinetic material transport. Examples of particularly preferred electrical controller systems are described in substantial detail in Published PCT Application No. 98/00707, previously incorporated herein by reference in its entirety for all purposes.

In addition to material transport systems, the microfluidic systems of the present invention also typically include an optical detection system. Optical detection systems used in the overall microfluidic systems of the invention typically include an optical train for directing an optical signal from the microfluidic channels of the device via the optical element integrated therein, to an appropriate light detector, such as a photodiode or photomultiplier tube. In particularly preferred aspects, the detector includes a light source for directing an appropriate amount of light energy at the channels of the device, in order to produce a measurable optical signal, e.g., fluorescence, absorbance, etc. Examples of appropriate light sources include, e.g., lasers, laser diodes, LEDs, high intensity lamps, and the like. The light energy from the light source is typically directed to the microscale channel of the device via the optical train, as well as the optical element integrated into the device, which are used to transmit the signal back to the detector.

All publications and patent applications referenced herein are hereby incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method for transmitting energy from or to at least one of two or more intersecting microscale channels disposed in a body structure of a microfluidic device comprising transmitting energy through an energy altering element located proximate to the at least one microscale channel in the body structure of the device, whereby at least a portion of said transmitted energy passing from or to the at least one microscale channel is transmitted through the energy altering element.

2. The method of claim 1 wherein said energy altering element includes a light altering optical element.

3. The method of claim 2, wherein the light altering optical element comprises a lens.

4. The method of claim 3, wherein the lens is selected from a magnifying lens, a demagnifying lens, and a collimating lens.

5. The method of claim 2, wherein the light altering optical element comprises a wavelength selective filter.

6. The method of claim 1 further comprising detecting at least a portion of the energy transmitted through the energy altering element with a detector positioned adjacent to said at least one microscale channel.

7. The method of claim 6 further comprising passing said transmitted energy through a detection window disposed on an exterior portion of the body structure prior to detecting said transmitted energy with said detector.

8. The method of claim 7 further comprising positioning the detector adjacent the detection window prior to detecting said transmitted energy with said detector.

9. The method of claim 8 wherein the detector is a light detector.

10. The method of claim 9 wherein the light detector is selected from a photomultiplier tube and a photodiode.

11. The method of claim 2, wherein the light altering optical element comprises a light altering optical coating disposed on an outer surface of the body structure.

12. A microfluidic device comprising a body structure, two or more intersecting microscale channels disposed in the body structure, and a means for altering light integrated into the body structure adjacent to at least one of the two or more intersecting microscale channels which is capable of transmitting or receiving light passing from or to the at least one microscale channel.

13. The device of claim 12 wherein the light altering means comprises a lens.

14. The device of claim 13, wherein the lens is selected from a magnifying lens, a demagnifying lens, and a collimating lens.

15. The device of claim 12, wherein the light altering means comprises a wavelength selective filter.

16. The device of claim 12 wherein the light altering means comprises an optical coating.

17. The device of claim 16 wherein the optical coating comprises one of wavelength selective filter, a spatial optical filter, and an antireflective coating.

18. A microfluidic device, comprising:
a first planar substrate having at least first and second opposing planar surfaces, and at least one microscale channel being fabricated into the first planar surface of the first substrate;
a second planar substrate having at least first and second opposing planar surfaces, said first planar surface of the second substrate being bonded to the first planar surface of the first substrate; and
a third planar substrate having at least a first planar surface and a second planar surface, the first planar surface of the third substrate being attached to one of the second planar surface of the first substrate or the second planar surface of the second substrate, said third planar substrate including a light altering optical element which is fabricated into the second planar surface of the third substrate.

19. The device of claim 18 wherein the light altering optical element comprises a lens.

20. The device of claim 18, wherein the lens is selected from a magnifying lens, a demagnifying lens, and a collimating lens.

21. The device of claim 18, wherein the light altering optical element comprises a wavelength selective filter.

22. The device of claim 18 wherein the light altering optical element comprises an optical coating.

23. The device of claim 22 wherein the optical coating comprises one of wavelength selective filter, a spatial optical filter, and an antireflective coating.

* * * * *